United States Patent [19]
Benton

[11] Patent Number: 6,054,031
[45] Date of Patent: *Apr. 25, 2000

[54] COMPOSITE CHANNEL JUNCTION

[75] Inventor: Barry W. Benton, Orange, Calif.

[73] Assignee: Rosemount Analytical Inc., Irvine, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/685,794

[22] Filed: Jul. 24, 1996

Related U.S. Application Data

[63] Continuation of application No. 08/431,062, Apr. 28, 1995, abandoned.

[51] Int. Cl.[7] .......................... G01N 27/30; G01N 27/333
[52] U.S. Cl. ............................................ 204/435; 204/416
[58] Field of Search .................................. 204/435, 416, 204/418, 419, 420

[56] References Cited

U.S. PATENT DOCUMENTS

| | | | |
|---|---|---|---|
| Re. 31,333 | 8/1983 | Barben, II | 324/450 |
| 2,830,945 | 4/1958 | Keidel | 204/195 |
| 3,151,052 | 9/1964 | Arthur et al. | 204/195 |
| 3,208,926 | 9/1965 | Eckfeldt | 204/195 |
| 3,264,205 | 8/1966 | Leonard et al. | 204/195 |
| 3,281,348 | 10/1966 | Schumacher et al. | 204/195 |
| 3,298,944 | 1/1967 | Luck | 204/195 |
| 3,440,525 | 4/1969 | Cardeiro | 324/40 |
| 3,479,270 | 11/1969 | Petersen et al. | 204/195 |
| 3,492,216 | 1/1970 | Riseman et al. | 204/195 |
| 3,666,652 | 5/1972 | Krauer et al. | 204/195 |
| 3,708,411 | 1/1973 | Vanslette | 204/435 |
| 3,790,463 | 2/1974 | Gealt | 204/195 |
| 4,002,547 | 1/1977 | Neti et al. | 204/435 |
| 4,112,352 | 9/1978 | Barben, II | 324/30 |
| 4,128,468 | 12/1978 | Bukamier | 204/195 |
| 4,162,211 | 7/1979 | Jerrold-Jones | 204/195 |
| 4,218,299 | 8/1980 | Lindell et al. | 204/195 F |
| 4,235,688 | 11/1980 | Sudrabin et al. | 204/195 |
| 4,282,081 | 8/1981 | Arrance | 204/435 |
| 4,390,406 | 6/1983 | Kato et al. | 204/435 |
| 4,664,772 | 5/1987 | Zuccari et al. | 204/400 |
| 4,913,793 | 4/1990 | Leonard | 204/433 |
| 5,147,524 | 9/1992 | Broadley | 204/433 |
| 5,152,882 | 10/1992 | Benton | 204/435 |
| 5,346,606 | 9/1994 | Christner et al. | 204/433 |

FOREIGN PATENT DOCUMENTS

| | | |
|---|---|---|
| 1 597 628 | 9/1981 | United Kingdom . |
| WO 94/06003 | 3/1994 | WIPO . |

OTHER PUBLICATIONS

Advertisement describing a product believed to be available since 1977, "Now the Remarkable Ross pH Electrode is Unbreakable", Orion Research date unavailable.

"Improvements in the Performance of Reference Electronics", SIRA, by Gawthrope, Simpson, Smurthwaite, Mar., 1979.

*Primary Examiner*—T. Tung
*Attorney, Agent, or Firm*—Westman, Champlin & Kelly, P.A.

[57] ABSTRACT

An electrochemical sensor structure includes a housing having an inner surface defining a housing cavity. The sensor also has an inner body having an outer surface. The outer surface of the inner body and the inner surface of the housing have engaging portions which directly engage one another to form a channel therebetween. The channel defines an ionic junction in the sensor.

19 Claims, 4 Drawing Sheets

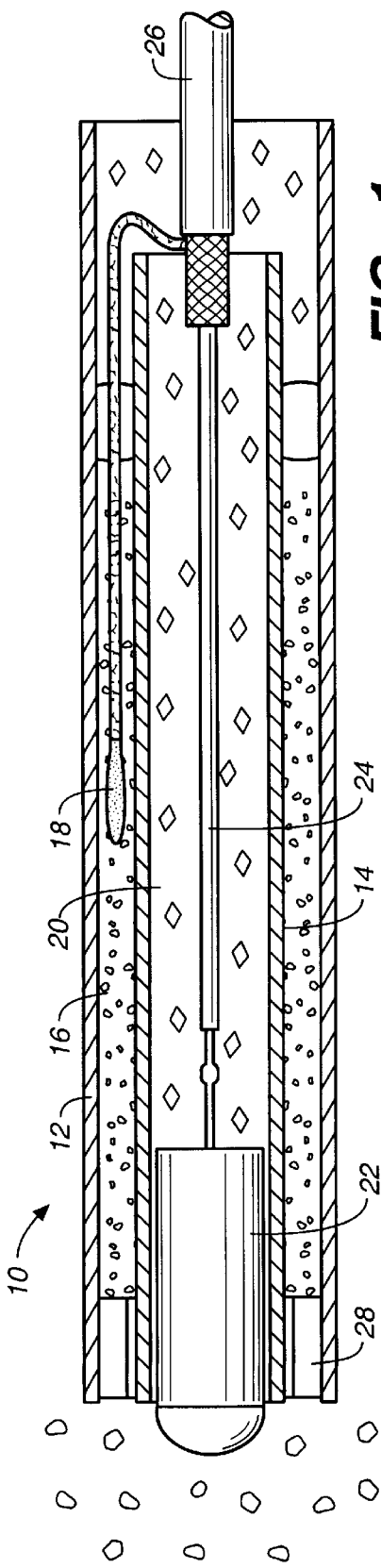
FIG._1 (PRIOR ART)
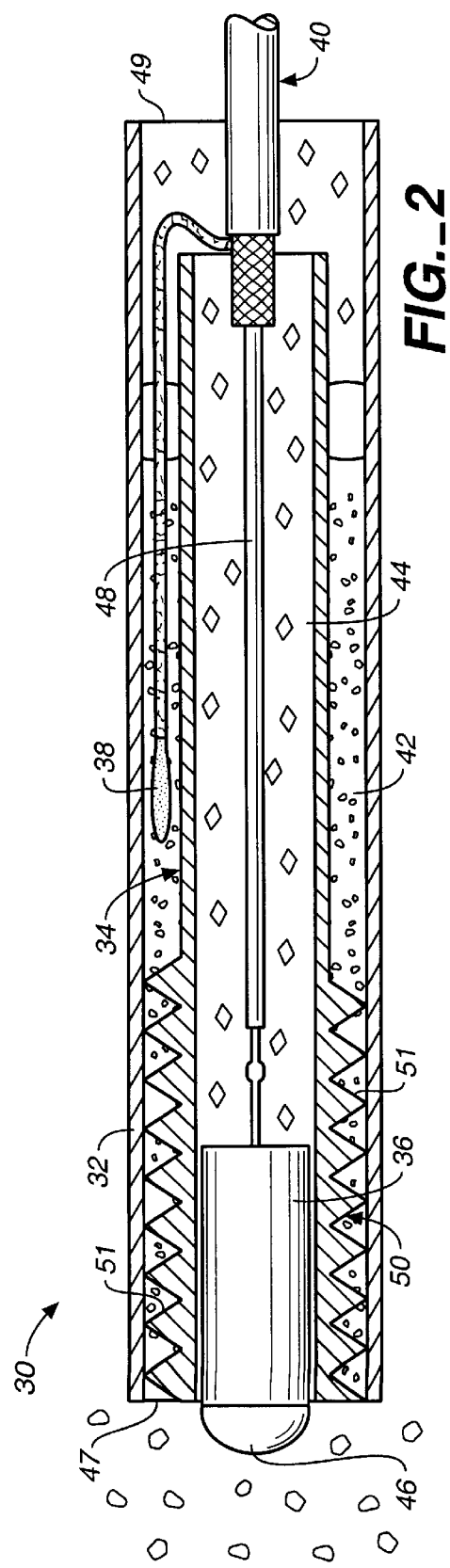
FIG._2

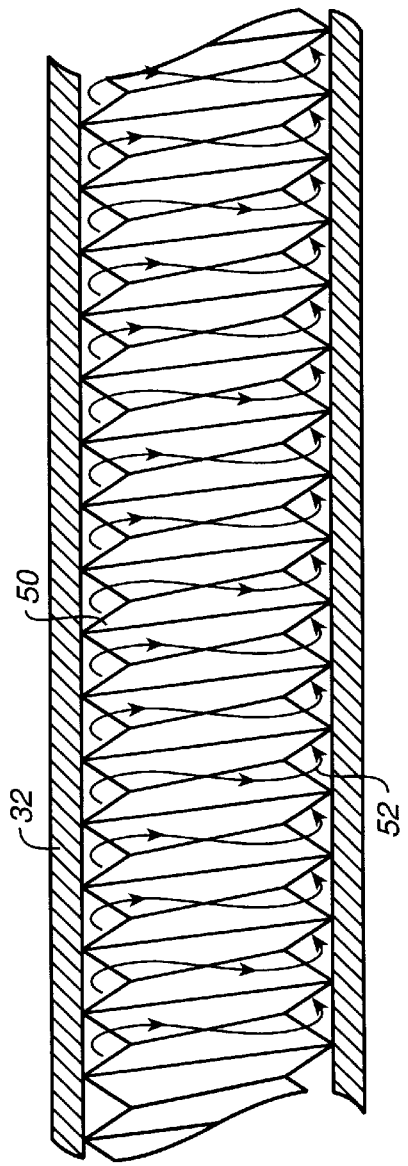
FIG._3
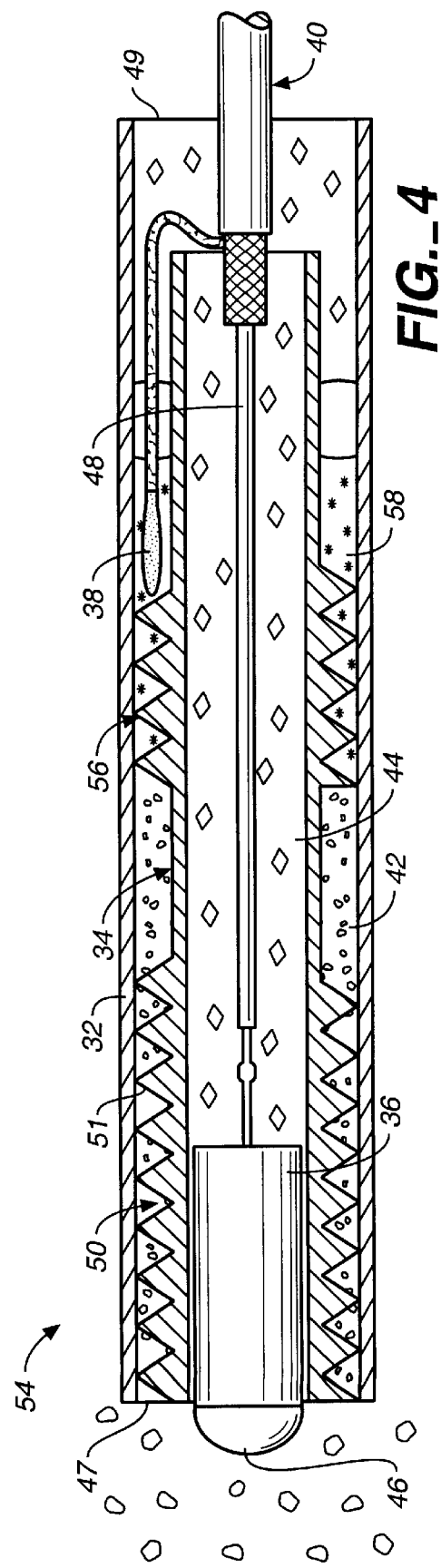
FIG._4

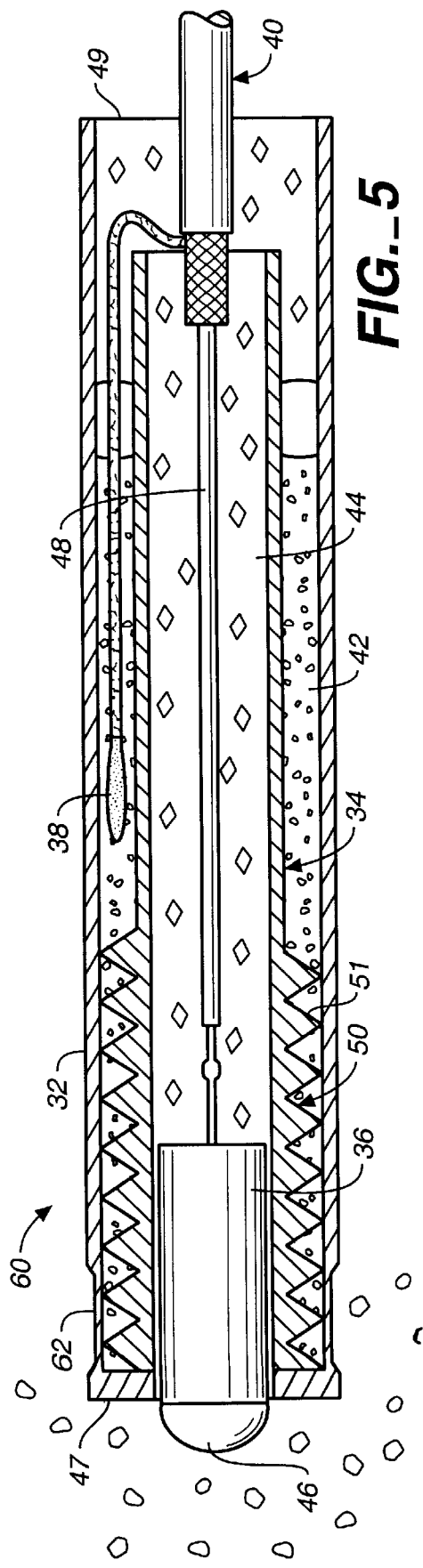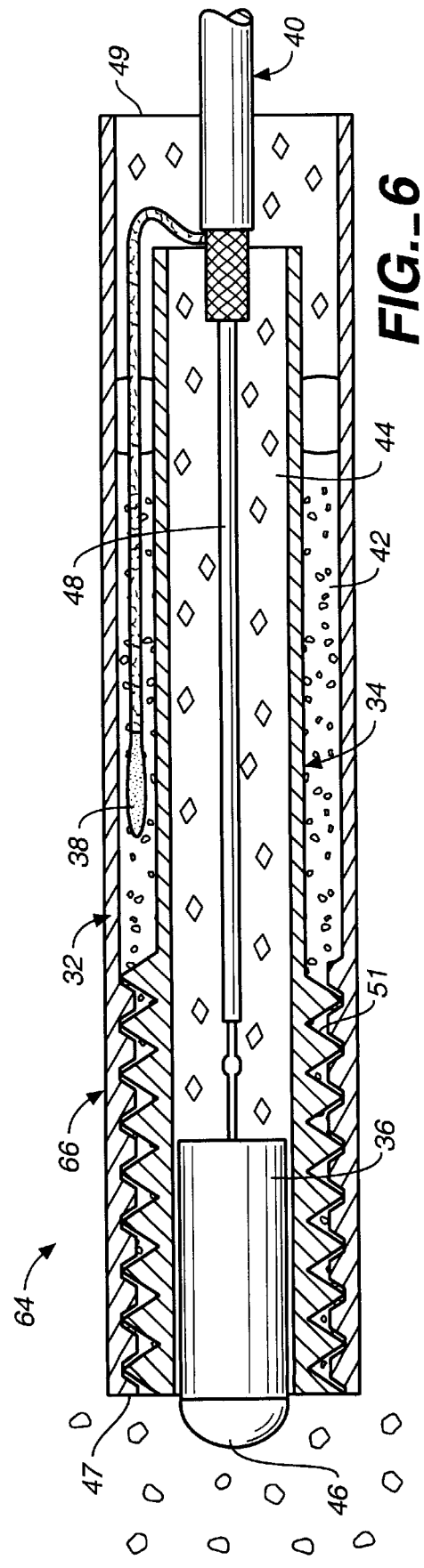

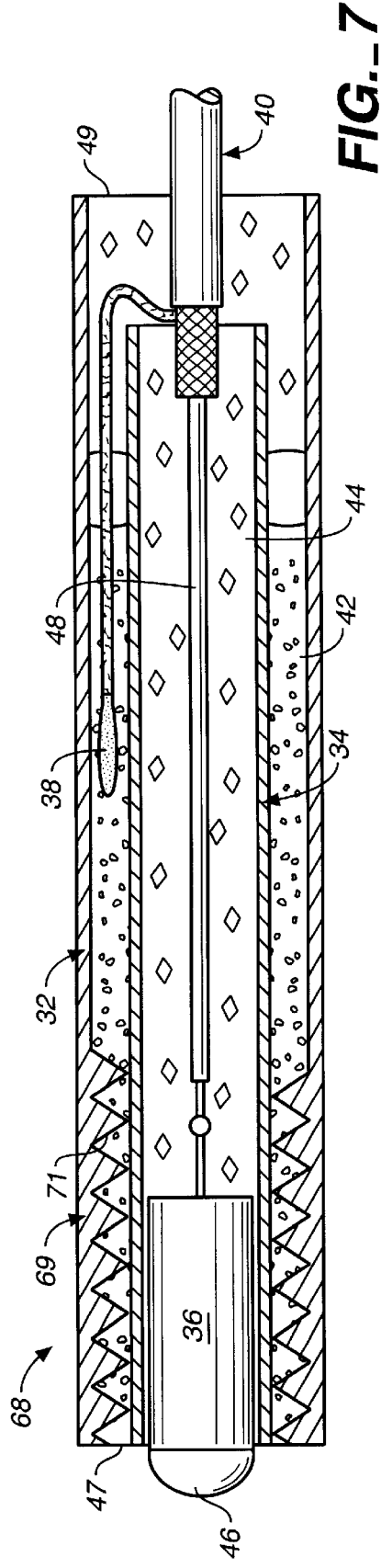
FIG._7
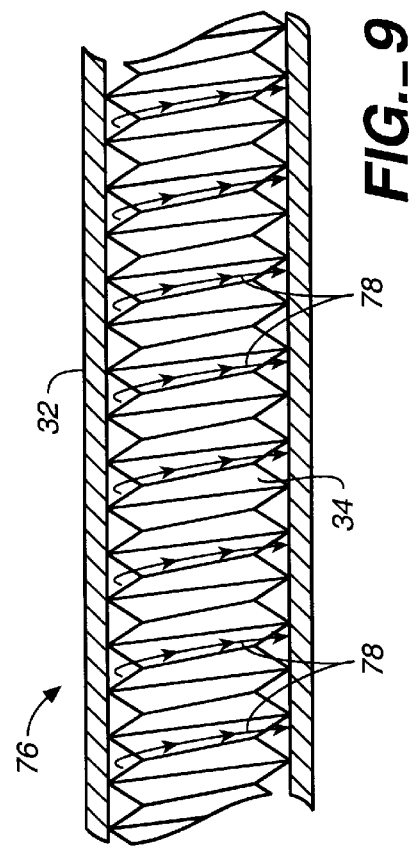
FIG._9
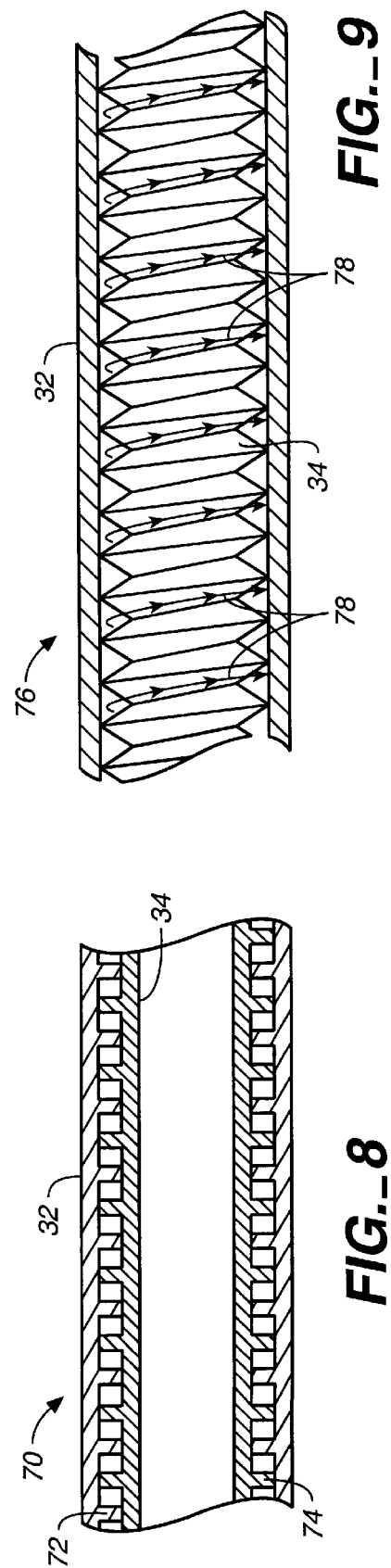
FIG._8

6,054,031

COMPOSITE CHANNEL JUNCTION

This is a continuation of application Ser. No. 08/431,062, filed Apr. 28, 1995, now abandoned.

BACKGROUND OF THE INVENTION

The present invention deals with sensors. More specifically, the present invention deals with a junction in a sensor which provides continuity between one solution and another solution.

Electrochemical sensors are commonly used to sense characteristics of a solution of interest. Conventional electrochemical sensors typically have an outer housing which defines a cavity filled with an internal or reference solution. A reference electrode is disposed within the reference solution. In addition, conventional electrochemical sensors typically have an inner body or housing, disposed within the inner cavity of the outer housing, which supports an ion selective electrode. The ion selective electrode extends out from within the cavity defined by the outer housing to contact a solution of interest to be analyzed.

A reference junction is commonly used in an attempt to substantially seal the cavity defined by the outer housing, other than where the ion selective electrode exits the cavity, so that the reference solution does not mix with, and become diluted by, the solution of interest. The reference junction maintains ionic communication between the reference solution and the solution of interest to enable accurate electrochemical measurements.

A disadvantage of such electrochemical sensors is limited useful lifetime as a result of degradation of the reference electrode due to ion exchange between the retained solution and the solution of interest. Prior attempts to extend the useful life involve modifying the electrochemical reference junction between the internal solution and the solution of interest. However, these attempts have typically required a discrete, specific junction component which is in addition to the outer housing and the other components required by the electrochemical sensor.

Such prior junctions provide an ionic leak between the internal solution and the solution of interest. The prior junctions have included an orifice, bundles of minuscule tubes which provide means of ionic migration, matrices of grains or open cells, and ion permeable membranes or solids, all of which provide an ionic leak between the internal solution and the solution of interest. These potential solutions have a disadvantage in that they require a separate, discrete component to be used in forming the ionic reference junction in the electrochemical sensor.

A number of these solutions have other deficiencies as well, such as difficulty of manufacture and fragility in industrial applications.

SUMMARY OF THE INVENTION

An electrochemical sensor structure includes a housing having an inner surface defining a housing cavity. The sensor also has an inner body having an outer surface. The outer surface of the inner body and the inner surface of the housing have engaging portions which directly engage one another to form a channel therebetween. The channel defines an ionic junction in the sensor.

BRIEF DESCRIPTION OF THE DRAWINGS

FIG. 1 is a side sectional view of an electrochemical sensor according to the prior art.

FIG. 2 is a side sectional view of one embodiment of an electrochemical sensor according to the present invention.

FIG. 3 is an enlarged view of a portion of the sensor shown in FIG. 2.

FIG. 4 is a side sectional view of a second embodiment of an electrochemical sensor according to the present invention.

FIG. 5 is a side sectional view of a third embodiment of an electrochemical sensor according to the present invention.

FIG. 6 is a side sectional view of a fourth embodiment of an electrochemical sensor according to the present invention.

FIG. 7 is a side sectional view of a fifth embodiment of an electrochemical sensor according to the present invention.

FIG. 8 is a side sectional view of another embodiment of a junction according to the present invention.

FIG. 9 is a side sectional view of another embodiment of a junction according to the present invention.

DETAILED DESCRIPTION OF THE PREFERRED EMBODIMENTS

FIG. 1 is a side sectional view of a prior art electrochemical sensor 10. Sensor 10 includes outer housing 12, inner body 14, reference electrode 18, ion selective electrode 22, cable assembly 26 and junction member 28. Outer housing 12 defines an inner cavity 16 in which inner body 14 is disposed. Cavity 16 is typically filled with an internal (or reference) solution within which reference electrode 18 is provided. Inner body 14 defines an inner portion 20 and supports an ion selective electrode 22. The remainder of inner portion 20 is filled with an inert back-fill material.

Ion selective electrode 22 extends from within housing 12 to contact a solution of interest. Ion selective electrode 22 also has conductors or other communication means 24 extending into cable assembly 26. Similarly, reference electrode 18 is coupled to cable assembly 26 by a conductor or other suitable means.

The reference junction between internal solution housed in cavity 16, and the solution of interest is formed by discrete junction member 28. Junction member 28 is disposed about the outer periphery of inner body 14 and has an outer dimension which closely approximates the inner surface of housing 12 to form a tight, frictional fit. In prior electrochemical sensors, such as sensor 10, the discrete junction component 28 has typically been formed of wood, grains, a semi-permeable membrane, or one or more minuscule tubes or capillaries. Having junction component 28 formed of a discrete component increases both assembly time and production costs.

Further, having the discrete junction or plug formed of semi-permeable material is undesirable. A semi-permeable material or electrolyte allows the passage of only some, or selected, substances. When used in an electrochemical reference electrode, some charged ions are retained by the semi-permeable junction resulting in a build-up of charge in the junction or electrolyte. This causes erroneous electrode potentials.

FIG. 2 is a side sectional view of an electrochemical sensor 30 according to the present invention. Sensor 30 includes an outer housing 32, inner body 34, ion selective electrode 36, reference electrode 38 and cable assembly 40. Housing 32 has a first axial end 47 and a second axial end 49 and defines an inner cavity 42 which is preferably filled with an internal or reference solution. Reference electrode 38 is disposed in the internal solution in cavity 42 between the inner surface of housing 32 and the outer surface of inner body 34.

Inner body 34 defines an interior bore 44 which typically has a first portion filled with an inert back-fill material and a second portion supporting ion selective electrode 36. Ion selective electrode 36 is supported such that it has a sensing surface 46 which preferably extends out from within housing 32 to contact a solution of interest. Ion selective electrode 36 is also coupled to cable assembly 40 by appropriate conductors 48. Reference electrode 38 is also coupled to cable assembly 40 by appropriate conductors.

FIG. 2 also shows that inner body 34 has an outer surface portion 51 generally located in the area of junction 50. Surface portion 51 preferably has a radial outer surface formed in the shape of a thread having a triangular cross-section. The outer peripheral dimension of the thread closely approximates the dimension of the inner surface of housing 32 so that the outer radial portion of the thread tightly engages the inner surface of housing 32. The thread on surface portion 51 obstructs the otherwise open process end 47 of housing 32 and forms a simple, small orifice configured as a long, helical channel by abutment of the outer radial portion of the thread against the inner surface of housing 32.

This helical channel provides a reduced cross-sectional area path between the solution of interest and reference electrode 38, and an increased path length between the solution of interest and the internal solution in cavity 42. This increased path length retards loss of the internal solution to the solution of interest, and also retards dilution of the interior solution by the solution of interest. The helical junction 50 thereby protects the sensitive reference electrode 38 from degradation and extends the stable life of electrode 38 and sensor 30.

It is worth noting that, in the preferred embodiment, helical junction 50 does not exist as a separate, discrete component. Rather, the junction exists as a filament-like helix of internal solution filling a void between the outer surface of body 34 and the inner surface of housing 32. This reduces both cost and assembly time over that required by prior electrochemical sensors which implemented the junction using an additional, discrete component.

The void defining the helical junction 50 is preferably filled with an appropriate internal junction material such as a solution or a solid material appropriate to the particular function of the electrochemical sensor 30. The internal junction material is preferably a permeable material. By permeable, it is meant that the junction material is generally porous to solids and solutes. In a preferred embodiment, the junction material is a gel or solid electrolyte material which is physically "thick" or "tight" to slow the general mobility of ions. However, the junction material is preferably not selective, or is minimally selective to avoid the build-up of an undesirable electrode potential. The inert back-fill material can be any suitable material and is preferably used to close end 49 of housing 32 through which cable assembly 40 extends.

FIG. 3 is an enlarged view of surface portion 51 of inner body 34 and a corresponding cross-sectional portion of housing 32. FIG. 3 better illustrates that surface portion 51 is formed as a simple helical screw thread and forms helical junction 50 which provides ion continuity between the solution of interest and reference electrode 38. The entire length of the helical channel or junction 50 is better illustrated by arrows 52 in FIG. 3 which are shown following the junction.

FIG. 4 shows a second embodiment of an electrochemical sensor 54 according to the present invention. Electrochemical sensor 54 is similar to electrochemical sensor 30, and corresponding items are similarly numbered. However, electrochemical sensor 54 includes a second ionic junction generally indicated by reference numeral 56. In the area of junction 56, the outer surface of inner body 34 is shaped similar to surface portion 51. In other words, the outer surface of inner body 34 in the area of junction 56 is formed with a triangular cross-section and as a helical screw thread.

The outer periphery of the helical screw thread at junction 56 has a dimension which closely approximates the dimension of the inner surface of housing 32 to define a second helical passageway, and to thereby define a second helical junction channel. In this preferred embodiment, the inner cavity 58 in the area of reference electrode 38 is filled with the internal or reference solution. The inner cavity 42 in the area between junctions 50 and 56 is filled with a permeable double junction electrolyte solution. Both of the solutions are chosen as appropriate to the particular function of sensor 54.

FIG. 5 shows another embodiment of the present invention. Sensor 60 is similar to sensor 30 shown in FIG. 2, and similar items are similarly numbered. However, sensor 60 also includes an integral junction 62. Integral junction 62 is preferably formed integrally proximate end 47 of housing 32. In the embodiment shown in FIG. 5, the helical screw thread forming junction 50 provides mechanical support for integral junction 62 in housing 32. Integral junction 62 is preferably formed by simply thinning the outer wall of housing 32 in the area of junction 62. When thinned sufficiently, and made of a suitable material, such as a glass fiber loaded thermoplastic more particularly described in U.S. Pat. No. 5,152,882, the outer wall of housing 32 becomes ion permeable to permit ionic transfer between the solution of interest external to junction 62 and the internal solution in junction 50.

It will be appreciated that integral junction 62 could also be used in sensor 54 shown in FIG. 4. This would result in the implementation of an integral junction, double junction sensor.

FIG. 6 shows yet another embodiment of the present invention. Sensor 64 is similar to sensor 30 shown in FIG. 2, and similar parts are similarly numbered. However, sensor 64 defines a junction 66 which also includes a contour on the inner surface of housing 32 in the area of junction 66. In the embodiment shown in FIG. 6, the contour on the interior surface of housing 32 in the area of junction 66 is formed in the shape of a truncated thread. This allows the threaded outer surface 51 of inner body 34 to nest and lock within the threads on the inner surface of housing 32, thus enhancing the stability of inner body 34 within housing 32.

FIG. 7 shows yet another embodiment of the present invention. Sensor 68 is similar to sensor 30 shown in FIG. 2, and similar items are similarly numbered. However, inner body 34 of sensor 68 is smooth throughout its entire length. Channel junction 69 in sensor 68 is formed by a screw thread 71 formed on the inner surface of housing 32. Screw thread 71 has an inner diameter which closely approximates the outer diameter of the smoothly contoured outer surface of inner body 34. Thus, while the junction 69 is still a helical channel junction formed by the abutment of housing 32 against inner body 34, the threaded structural portion is formed on housing 32, rather than on inner body 34.

FIG. 8 shows another embodiment of the present invention. FIG. 8 shows an enlarged view of a portion of a junction 70 formed by generally opposing portions of inner body 34 and housing 32. FIG. 8 shows that housing 32 is provided with an inwardly extending rectangular thread 72, and inner body 34 is provided with an outwardly extending rectangular thread 74. Threads 72 and 74 abut opposing portions of inner body 34 and housing 32, respectively, to form a channel defining ionic junction 70.

FIG. 9 shows yet another embodiment of a junction according to the present invention. FIG. 9 shows a junction 76 similar to that shown in FIG. 3, except that junction 76 shown in FIG. 9 is comprised of two, nested and parallel helical channels preferably formed as a multiple start thread. Arrows 78 point out one of the two helical channels comprising junction 76.

The junctions formed by the present invention provide a long channel having a relatively small cross-section for providing ionic continuity between one solution and another. By providing a small transverse area with a very long and tortuous channel length, the junction of the present invention increases ion transit time through the channel. Thus, ion exchange between solutions separated by the channel is limited or significantly slowed.

While the cross-sectional area of the channel is small relative to its length, the length is great enough so that it reduces or limits ion exchange, and the cross-sectional area of the channel can be fairly large (larger than a capillary). This makes the channel substantially resistant to plugging.

It is also worth noting that the channels of the present invention need not even be microscopic, but are preferably quite distinct and readily visible to the naked eye. Due to the increase in length of the channel, the transverse area of the channel may be as large as practicable for the size of the sensor and for the characteristics of the solution of interest and the internal solution. The channel should simply be sized to operably retain the internal solution or solutions, to ensure ionic continuity between desired solutions, and to retard electrode degradation and solution concentration loss.

Further, the large length to transverse area ratio of the junction according to the present invention improves performance by reducing junction potential and impedance over that found in conventional, mechanical junctions.

It should also be noted that, while the channel according to the present invention is shown in one preferred embodiment as having a triangular cross-section, the shape is generally and preferably determined by several considerations, such as the ease of parts fabrication, the ease of assembly, and other common design parameters which would affect the shape. Thus, the shape can be any other shape which is suitable to the particular use.

Further, while the channel according to the present discussion is shown as generally helical, it is to be understood that the channel could be formed of other geometries, such as a flat spiral, nested spiral cylinders (which need not have a circular cross-section), an irregular shape, such as a labyrinth, or another suitable shape. Further, multiple channels may be used, rather than a single channel.

In addition, the inner body can be locked to the outer housing as shown in FIG. 6. This increases the compatibility of the sensor with rough and severe environments.

The outer housing 32 and inner body 34 are preferably molded or cast. Therefore, forming the necessary contours on the parts to define the channel according to the present invention adds little, if any, additional expense to the sensor structure. This is a significant improvement over prior sensors which required a discrete junction component.

Finally, it should be noted that the sensor according to the present invention can be utilized with any number of types of sensors, such as a specific ion sensor, a pH sensor, a dissolved gas sensor, or other electrochemical electrodes or sensors requiring such a junction.

Although the present invention has been described with reference to preferred embodiments, workers skilled in the art will recognize that changes may be made in form and detail without departing from the spirit and scope of the invention.

What is claimed is:

1. An electrochemical sensor comprising:
   a first member including a first surface;
   a second member including a second surface at least partially defining a cavity the first member being sized to fit into the cavity of the second member to form an electrolytic chamber between the first surface of the first member and the second surface of the second member;
   a non-porous electrolytic junction formed of an ion permeable member closing the electrolytic chamber and separating the electrolytic chamber from the process solution; and
   a wickless helical channel along a portion of the electrolytic chamber formed between the first and second members, wherein a portion of one of the first and second surfaces includes a helical surface structure, the first and second members being sized so that the helical surface structure tightly engages a generally smooth surface of a portion of the other of the first and second surfaces to form the wickless helical channel being between the first and second surfaces.

2. The electrochemical sensor of claim 1 wherein the electrolytic chamber is filled with an electrolytic gelled material.

3. The electrochemical sensor of claim 1 wherein the helical surface structure is formed of a helical screw thread.

4. The electrochemical sensor of claim 1 wherein the helical surface structure is formed of a rectangular thread.

5. The electrochemical sensor of claim 1 wherein the non-porous electrolytic junction is formed integral with the second member.

6. The electrochemical sensor of claim 1 wherein the ion permeable member is formed of a fiber loaded molded thermoplastic material.

7. The electrochemical sensor of claim 1 wherein the ion permeable member is formed of a thinned portion of the second member.

8. The electrochemical sensor of claim 1 wherein the ion permeable member is aligned generally parallel to a longitudinal axis of the first and second members.

9. The electrochemical sensor of claim 1 wherein multiple spaced portions of one of the first and second surfaces include helical surface structures adapted to tightly engage a smooth surface of the other of the first and second surfaces.

10. The electrochemical sensor of claim 1 wherein the first member includes the helical surface structure.

11. The electrochemical sensor of claim 1 wherein the second member includes the helical surface structure.

12. An electrochemical sensor comprising:
   a first member including a first surface;
   a second member having a second surface at least partially forming a cavity, the first member being sized to fit into the cavity;
   an electrolytic chamber filled with a solid or gelled electrolytic material, the electrolytic chamber being formed between the first surface of the first member and the second surface of the second member;

a non-porous electrolytic junction formed of an ion permeable member;

a wickless helical channel between the electrolytic chamber and the electrolytic junction, the wickless helical channel being formed between the first and second members, wherein a portion of one of the first and second surfaces includes a helical surface structure, the first and second members being sized so that the helical surface structure tightly engages a generally smooth surface of the other of the first and second surfaces to form the wickless helical channel between the first and second surfaces.

13. An electrochemical sensor comprising:

a first member including a first surface;

a second member including a second surface at least partially forming a cavity, the first member being sized to fit into the cavity of the second member;

an electrolytic chamber between the first surface of the first member and the second surface of the second member;

a non-porous electrolytic junction formed of an ion permeable member; and a wickless helical channel separating the electrolytic chamber from the electrolytic junction and having opposed first and second portions, the first portion opened to the electrolytic chamber and the second portion opened to the electrolytic junction, the wickless helical channel being formed between the first and second members, wherein a portion of one of the first and second surfaces includes a helical surface structure, the first and second members being sized so that the helical surface structure tightly engages a generally smooth surface of a portion of the other of the first and second surfaces to form the wickless helical channel between the first and second surfaces.

14. The electrochemical sensor of claim 13 wherein the electrolytic chamber includes a reference electrode.

15. The electrochemical sensor of claim 13 wherein the ion permeable member is aligned generally parallel to a longitudinal axis of the first and second members.

16. The electrochemical sensor structure of claim 13 wherein the electrolytic chamber is filled with a solid or gelled electrolytic material.

17. The electrochemical sensor of claim 13 wherein the ion permeable member is formed of a thinned portion of the second member aligned generally parallel to a longitudinal axis of the first and second members.

18. The electrochemical sensor of claim 13 wherein the electrolytic chamber is an annular chamber formed between first and second members.

19. An electrochemical sensor comprising:

a first member including a first surface;

a second member having a second surface at least partially forming a cavity, the first member being sized to fit into the cavity;

an electrolytic chamber filled with a solid or gelled electrolytic material, the electrolytic chamber being formed between the first surface of the first member and the second surface of the second member;

a non-porous electrolytic function formed of an ion permeable member; and a wickless helical channel between the electrolytic chamber and the electrolytic function, the wickless helical channel being formed between the first and second members, wherein a portion of one of the first and second surfaces includes a helical surface structure, the first and second members being sized so that the helical surface structure tightly engages a generally smooth surface of a portion of the other of the first and second surfaces to form the wickless helical channel between the first and second surfaces;

a sensing electrode supported by the first member; and a reference electrode operably coupled to the electrolytic chamber.

* * * * *

UNITED STATES PATENT AND TRADEMARK OFFICE
CERTIFICATE OF CORRECTION

PATENT NO. : 6,054,031
DATED : April 25, 2000
INVENTOR(S) : Benton

It is certified that error appears in the above-identified patent and that said Letters Patent is hereby corrected as shown below:

Column 8, line 25, after "electrolytic" delete "function" and insert
--junction--.

Signed and Sealed this

Third Day of April, 2001

Attest:

NICHOLAS P. GODICI

*Attesting Officer*   Acting Director of the United States Patent and Trademark Office